United States Patent [19]

Goldberg et al.

[11] Patent Number: 4,624,659

[45] Date of Patent: Nov. 25, 1986

[54] SYRINGE WITH PRESSURE SENSING MEANS

[76] Inventors: Edward M. Goldberg, 225 Maple Hill Rd., Glencoe, Ill. 60022; Seymour Bazell, 9235 North Latrobe, Skokie, Ill. 60077

[21] Appl. No.: 779,492

[22] Filed: Sep. 24, 1985

[51] Int. Cl.⁴ .............................................. A61M 5/00
[52] U.S. Cl. .................................... 604/121; 604/227; 222/47
[58] Field of Search ............... 604/121, 125, 108, 218, 604/227; 222/47

[56] References Cited

U.S. PATENT DOCUMENTS 1,643,531 9/1927 Wolf ..................................... 604/125
4,000,741 1/1977 Binard et al. ........................ 604/121

Primary Examiner—Stephen C. Pellegrino
Attorney, Agent, or Firm—Hosier & Sufrin, Ltd.

[57] ABSTRACT

An instrument for injecting and withdrawing fluids including an elastomeric membrane in communication with the chamber of the instrument from which fluids are injected or into which they are withdrawn, in which the membrane expands and contracts with increasing and decreasing pressure in the chamber, providing both a visual and a tactile indication of the pressure of injection or withdrawal, and a pressure relief.

18 Claims, 9 Drawing Figures

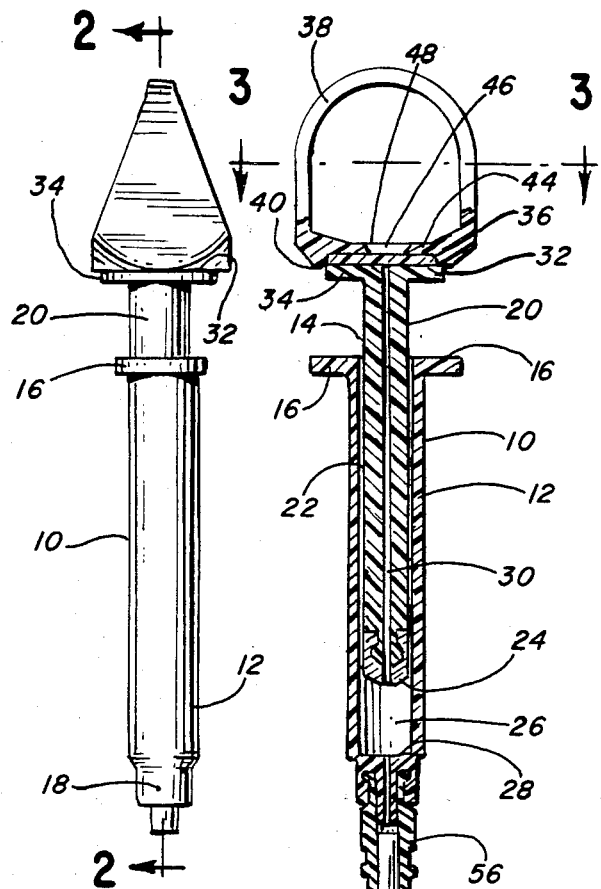
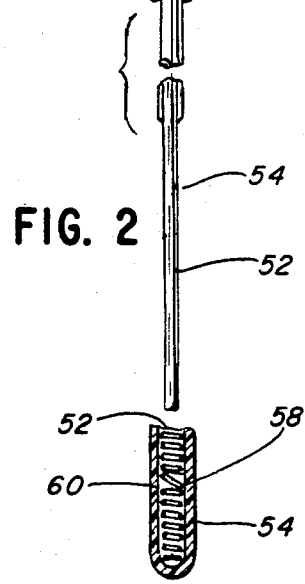
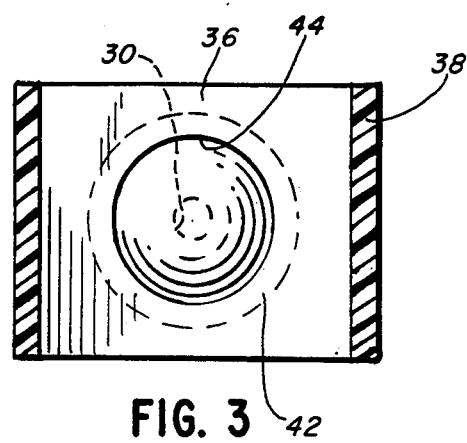
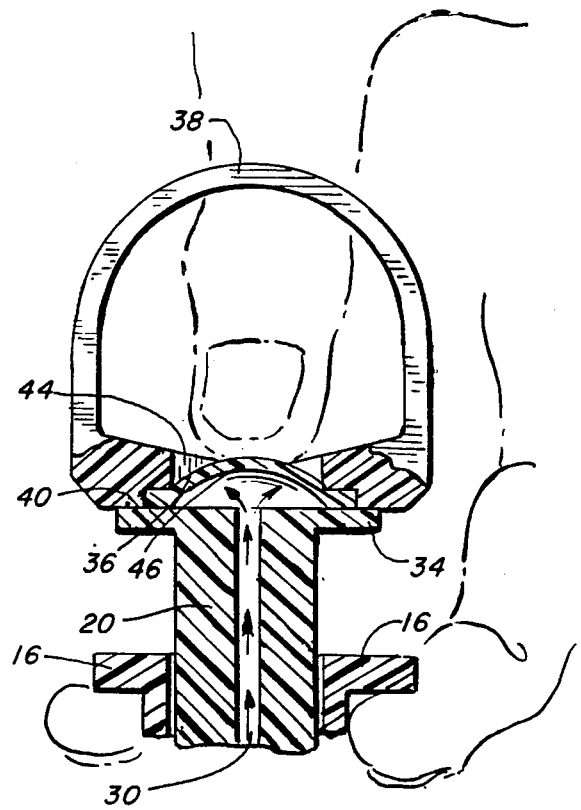

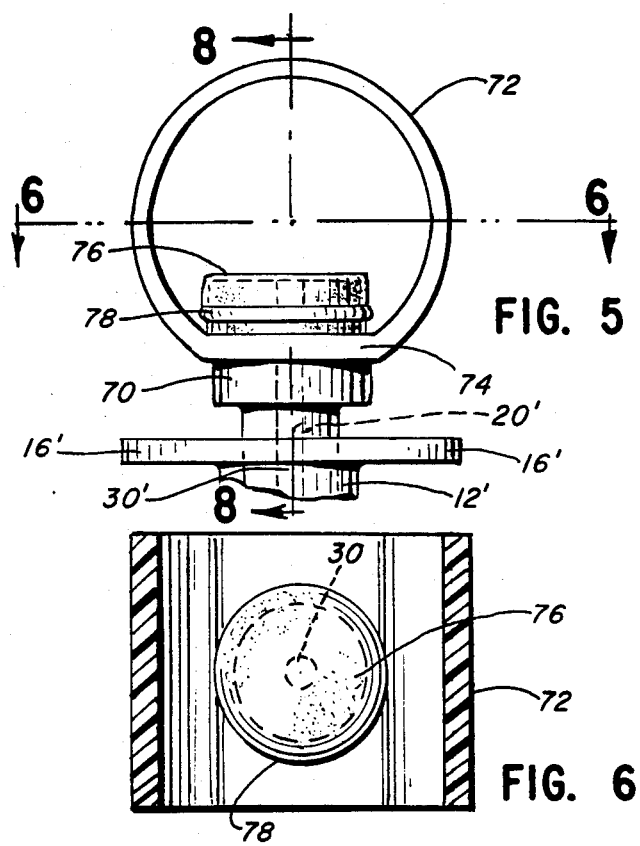
FIG. 5
FIG. 6
FIG. 7
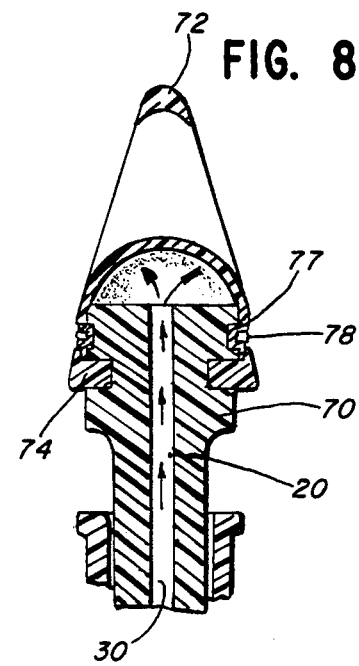
FIG. 8
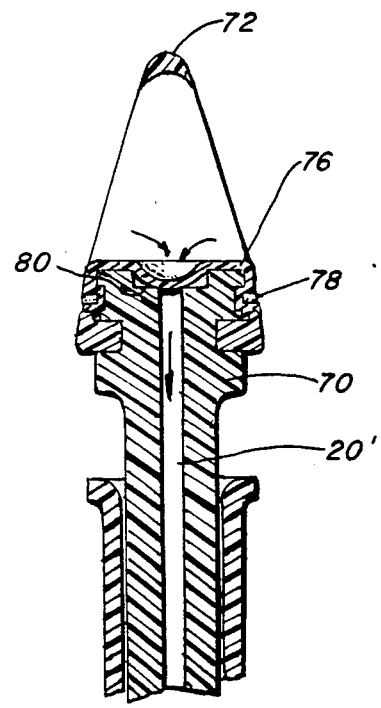
FIG. 9

SYRINGE WITH PRESSURE SENSING MEANS

BACKGROUND OF THE INVENTION

This invention relates generally to instruments for injecting or withdrawing fluids. More particularly this invention relates to syringes having means for sensing pressure on either injection or withdrawal of fluids.

Syringes of numerous types are used in the medical field for injecting and withdrawing fluids from cavities and vessels in the body, for subcutaneous injection, and for other purposes. The fundamental design of such syringes has not changed significantly over the years. Almost all such syringes have a hollow barrel, a plunger which is inserted into the barrel from one end, and a hollow tip at the other end of the barrel for receiving a cannula, a tube or other device for conducting fluid into or out of the syringe.

In many applications fluids must be injected or withdrawn without creating excessive positive or negative pressure. For example, the act of introducing fluids into a vessel or into a balloon that is positioned in a vessel or duct lumen transmits pressure to the vessel or duct wall. These transmitted forces can be damaging to the vessel or duct wall, causing architectural alterations and even occasionally wall disruption. It is critical that undue pressure be avoided when injecting fluid into small vessels in the body, particularly small vessels of infants, children and adults. Similarly, excessive pressure must be avoided in hydrostatic dilatation of free or in situ vein graphs for venous or arterial bypass procedures, and in the inflation of endotracheal, urinary, biliary, vascular and other balloon catheters.

The provision of means for sensing pressure applied on either injection or withdrawal of fluids by syringe would make it far easier to avoid the application of undue pressure. The provision of such pressure sensing means would have other important medical applications such as in procedures where the lumbar spinal canal must be penetrated by syringe while the cerebral spinal fluid pressure is monitored.

Embolectomy catheters, used to remove blood clots from blood vessels, comprise a new type of catheter into which fluid must be injected to inflate a balloon, where the need for avoiding the application of excessive pressure is acute. Such catheters are inserted through an incision into a blood vessel and moved with the catheter balloon deflated to a point beyond the clot, whereupon the balloon is inflated and the catheter is withdrawn pushing the clot ahead of it until it reaches the incision where it can be readily withdrawn. If excessive transmitted wall pressures and excessive wear stresses are applied to the vessel wall as the balloon is inflated or withdrawn, the vessel can be seriously damaged or even ruptured. If the balloon is severely over-inflated, it can, in rare instances, fragment leaving portions of the catheter in the vessel and creating the danger of obstructions in the vascular system.

U.S. Pat. No. 4,444,188 to the present inventors describes in one embodiment an embolectomy catheter in which the balloon is inflated by applying finger pressure directly to a resilient chamber integral with the catheter and in direct communication with the balloon. Squeezing the chamber inflates the balloon with air and thus the chamber provides the user with direct, tactile information regarding the fluid pressure of the inflated balloon, so that the user can react to excessive balloon pressure by relaxing the finger grip. While the approach of the '188 patent has found widespread acceptance, the provision of a syringe for filling the catheter with either air or liquid could enhance the operation of this device. Unfortunately, a conventional syringe would be woefully inadequate in this or any other application in which the user must quickly and accurately sense the gas or liquid pressure being applied by the syringe because in a conventional syringe the pressure signal is masked by the friction between the plunger and the inside wall of the barrel.

SUMMARY OF THE INVENTION

It is therefore an object of the present invention to provide a syringe with means for sensing pressure on either injection or withdrawal fluids.

Another object of the present invention is to provide an instrument for injecting into or withdrawing fluids from body vessels, cavities, and tissues, without creating excessive positive or negative pressure therein.

A further object of the present invention is to provide a syringe with pressure sensing means which can be used in the inflation of embolectomy, endotracheal, urinary, biliary, vascular and other balloon catheters and in hydrostatic dilatation of free or in situ vein graphs for venous or arterial bypass procedures.

Yet another object of the present invention is to provide a syringe with pressure sensing means which can be used to inflate embolectomy catheter balloons while providing a tactile and visual indication of the pressure in the system both in inflation of the balloon and as the balloon is drawn through a blood vessel.

A still further object of the present invention is to provide a syringe with means which serves both as a pressure relief mechanism and a sensor to prevent overdistention and potential damage to vessels or ducts into which fluid is being administered.

The present invention is therefore directed to an instrument for injecting and withdrawing fluids including a hollow barrel closed at one end and a plunger mounted in the barrel having a piston for sealingly engaging the inner surface of the barrel. A chamber is defined within the barrel between the end of the plunger and the closed end of the barrel, and a tip is provided in the closed end of the barrel for conducting fluid into and out of the chamber. Finally, sensing means are provided in fluid communication with the chamber for transmitting a tactile and visual indication of the pressure in the chamber.

In one important embodiment, the sensing means includes a longitudinal bore in the plunger and a elastomeric membrane at the top of the plunger which expands and contracts with changes in the pressure within the chamber effected by moving the plunger within the barrel.

The present invention thus solves the need and the art for a syringe which provides means for sensing pressure on either injection or withdrawal of fluids.

BRIEF DESCRIPTION OF THE DRAWINGS

The features of this invention which are believed to be novel are set forth with particularity in the appended claims. The invention, together with its objects and the advantages thereof, may be best understood by reference to the following description, taken in conjunction with the accompanying drawings, in which like reference numerals identify like elements in the several figures and in which:

FIG. 1 is a side elevation view of a syringe provided with a pressure-indicating membrane;

FIG. 2 is a cross-sectional view of the syringe shown in FIG. 1, taken on section line 2—2 of FIG. 1 with the syringe tip operatively connected to an embolectomy catheter which is shown in an enlarged cross-sectional view near its insertion end;

FIG. 3 is an enlarged plan view of a portion of the upper end of the syringe of FIG. 2, taken on section line 3—3 of FIG. 2;

FIG. 4 is a fragmentary, enlarged, cross-sectional view of the upper end of the syringe as depicted in FIG. 2 engaged by the fingers and thumb of the operator and showing the pressure-indicating membrane in an inflated condition;

FIG. 5 is an enlarged, fragmentary, front elevational view of the upper end of a syringe illustrating an alternate embodiment of the pressure-indicating membrane;

FIG. 6 is an enlarged plan view of a portion of the upper end of the syringe of FIG. 5, taken on section line 6—6 of FIG. 5;

FIG. 7 is an enlarged, fragmentary, front elevational view of the upper end of a syringe corresponding to FIG. 5 in which the membrane is depicted in an inflated condition;

FIG. 8 is an enlarged, cross-sectional view of the syringe of FIG. 5, taken on section line 8—8 of FIG. 5; and FIG. 9 is an enlarged, cross-sectional view of the syringe of FIG. 5 in which the plunger is being withdrawn from the barrel to produce a negative pressure in the system as indicated by the membrane which is being drawn onto an undercut threshold at the proximal end of the bore of the plunger.

DESCRIPTION OF THE PREFERRED EMBODIMENTS

Turning now to FIGS. 1 and 2, a plastic syringe 10 constructed in accordance with the present invention is illustrated. Although the syringe depicted is plastic, the present invention would find equal application with glass syringes. Syringe 10 comprises an elongated barrel 12 having an open proximal end 14 with opposite, radially outward extending arms 16 and a delivery tip 18 at its distal end.

A plunger 20, as best illustrated in the cross-sectional view of FIG. 2, is disposed within barrel 12, dimensioned to leave an annular passage 22 between the outer wall of the plunger and the inner wall of the barrel, so that the plunger can slide freely within the barrel. Plunger 20 has a resilient piston 24 at its distal end to seal against the inner wall of the barrel as the plunger is moved therein. Of course, sealing means other than a resilient piston could be used, such as the glass-to-glass seal obtained in many glass syringes.

A chamber 26 is defined in the barrel of the syringe because the distal end of piston 24 and the bottom 28 of the barrel. It is this chamber into which fluid (liquid or gas) is drawn by withdrawing the plunger from the barrel or from which fluid is expelled by advancing the plunger within the barrel, depending upon the intended application of the syringe.

The positive and negative pressure produced in chamber 26 by respectively advancing or withdrawing plunger 20 is transmitted through the plunger by way of an axial bore 30 which runs through piston 24 and the length of the plunger to its proximal end 32. At its proximal end, the plunger has an annular flange 34 bearing an elastomeric membrane 36 which seals off the proximal end of bore 30. As best illustrated in FIGS. 2 and 3, membrane 36 is held in place by a thumb loop 38 having an annular base surface 40 which is attached by conventional means such as by ultrasonic welding or solvent sealing to the top of annular flange 34 of the plunger, entrapping the edge 42 of the membrane in sealing engagement with the top of flange 34 under an annular lip 44, in the base of the thumb loop.

The central portion 46 of membrane 36, which normally lies in a plane as illustrated in FIG. 2, is free to bulge upwardly into an opening 48 in the thumb loop (FIG. 4). Thus, when the syringe is in communication with a vessel, cavity, catheter, etc. and therefore part of a closed system, and the plunger is advanced in the barrel by the operator with his or her thumb in thumb loop 38 and index and forefinger behind arms 16, a positive pressure is produced in chamber 26 and transmitted through bore 30 to membrane 36, which bulges upwardly through indicator opening 48. The bulging membrane engages the pad of the operator's thumb, providing a tactile as well as a visual signal to the operator of the pressure in the system. The bulging membrane acts as well as a pressure relief mechanism for the system.

As already noted, the above syringe can be used in a wide variety of applications including to inflate the balloon of an embolectomy catheter of the type generally shown in U.S. Pat. No. 4,444,188. This embolectomy catheter includes, as best seen in FIG. 2, an elongated coil spring support 52 which is covered with an elongated sheath 54 of a resilient material such as silicone rubber, and an open luer-type connector 56 for sealingly engaging syringe tip 18. An axially sprung coil 58 of spring support 52 provides an opening for fluid pressure to be applied to the inner wall of a balloon section 60 which, when uninflated, lies in the plane of sheath 54, and when inflated, bulges outwardly forming a sleeve-like drag balloon which is free to be distorted axially as well as radically under axial force applied to the catheter.

Advancing the plunger 20 in the syringe barrel creates fluid pressure in the catheter forcing the balloon to expand while membrane 36 responds to the same fluid pressure. The resilience of the membrane is chosen to insure that when the membrane bulges through indicator opening 48 encountering the pad of the operator's thumb, the maximum desirable balloon inflation will just be exceeded. The bulging balloon thus provides the operator with both a tactile and a visual indication that the plunger must be backed out slightly in order to avoid damage to the vessel through which the catheter is being drawn.

As the catheter is manually pulled through the blood vessel, the inflated balloon will expand or contract in accord with the confining pressure placed on it by the walls and contents of the blood vessel. The resulting fluctuating pressure in the system will be transmitted through the catheter to membrane 36 to provide the operator with a continuing indication of changes in the pressure in the system, so that the user may make an informed decision to increase or decrease the pressure by withdrawing or further depressing the syringe plunger.

FIGS. 5–9 show an alternate embodiment of the present invention in which the resilient membrane is affixed in a different fashion from that depicted in the earlier figures, while the other features of the earlier figures remain unchanged.

Turning first to FIG. 5, the proximal end of barrel 12' is depicted with radially protruding fingers 16'. Plunger 20' is shown, inserted in the barrel, with axial bore 30' extending through the length of the plunger and a resilient piston at its distal end (not shown). A flange 70 is provided at the proximal end of the plunger, with an intermediate circumferential groove for mating with a corresponding semi-circular slot (not shown) in the base 74 of thumb ring 72.

An elastomeric membrane 76 is affixed over the proximal end of plunger flange 70. A second circumferential groove 77 (FIG. 8) is formed in the outer surface of the flange, and membrane 76 is stretched over the plunger end past this circumferential groove, so that retaining means such as a ring type circular clamp 78 or a winding of thread may be applied to groove 77 to sealingly engage or hold the membrane in place.

Membrane 76 performs the same pressure sensing function as described in connection with the prior embodiment, although its larger effective area provides a more sensitive tactile indication of pressure. Indeed the device depicted in this second embodiment can be used in any application to which the first is applicable, inflating to produce a tactile and visual pressure indication as shown in FIGS. 7 and 8.

In another embodiment of the invention, membrane 76 can serve as an indicator of negative pressure in the system. This is illustrated in FIG. 9, where membrane 76 is shown being drawn into axial-bore 20' which is undercut to form a threshold 80. Thus, as fluid is withdrawn through the syringe the membrane is drawn down onto the threshold which provides both a visual as well as a tactile signal of negative pressure in the system.

The membrane used in the invention may be made of any soft elastomeric material, such as natural latex rubber, silicone rubber, or sufficiently elastic plastisols. While the membrane is depicted as located at the proximal end of the plunger, it would, of course, be possible to place the membrane at other locations, such as over an aperture on the side of the plunger, where the plunger is elongated to permit aperture and membrane to be clear of the syringe barrel when the plunger is in the closed position.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What we claim is:

1. An instrument for injecting and withdrawing fluids while providing an indication of the pressure applied thereby, comprising:
   a hollow barrel which is closed at its distal end and open at its proximal end:
   a plunger mounted in said barrel for longitudinal movement therein,
   said plunger including piston means for sealingly engaging the inner surface of said barrel, said plunger further defining a chamber within said barrel between said distal end of said barrel and said piston means;
   hollow tip means, disposed at said distal end of said barrel, for conducting fluid into and out of said chamber; and,
   sensing means, in fluid communication with said chamber and disposed adjacent said proximal end of said barrel, for indicating the pressure in said chamber.

2. The instrument of claim 1 wherein said plunger includes an axial bore in fluid communication with both said chamber and said sensing means.

3. The instrument of claim 1 wherein said sensing means includes means for providing both a tactile and a visual indication of the pressure in said chamber.

4. The instrument of claim 1 wherein said sensing means includes elastomeric means which expands and contracts with increasing and decreasing pressure in said chamber.

5. The instrument of claim 3 wherein said sensing means includes as well means for relieving pressure in said chamber.

6. The instrument of claim 4 wherein said plunger includes an axial bore between said chamber and the proximal end of said plunger and said elastomeric means comprises an elastomeric membrane sealing said proximal end of said plunger.

7. The instrument of claim 4 wherein said plunger includes a bore between said chamber and an aperture adjacent the proximal end of said plunger and said elastomeric means comprises an elastomeric membrane sealing said aperture.

8. The instrument of claim 6 wherein said elastomeric membrane is made of a material chosen from the group consisting of latex rubber, silicone rubber and elastic plastisols.

9. The instrument of claim 6 wherein said membrane is made of latex rubber.

10. The instrument of claim 6 wherein a thumb loop is provided at the proximal end of said plunger, said thumb loop including means for entrapping the edge of said membrane in sealing engagement with the proximal end of said plunger.

11. The instrument of claim 6 wherein said plunger includes, adjacent its proximal end, a circumferential groove, said membrane extends over said proximal end of said plunger past said circumferential groove, and retaining means are applied at said groove to engage said membrane.

12. The instrument of claim 6 wherein said bore includes a threshold below said membrane for receiving said membrane when negative pressure in said chamber falls below a predetermined level.

13. A syringe for injecting and withdrawing fluids from the body while providing an indication of the pressure applied thereby, comprising:
   a hollow barrel which is closed at one end;
   a plunger mounted in said barrel for longitudinal movement therein, said plunger including piston means for sealingly engaging the inner surface of said barrel and an axial bore running from the distal to the proximal end of said plunger, said plunger further defining a chamber within said barrel between said closed end of said barrel and the distal end of said piston means;
   hollow tip means, disposed at said closed end of said barrel, for conducting fluid into and out of said chamber; and,
   an elastomeric membrane closing the proximal end of said bore in said plunger, whereby said membrane is inflated with increasing pressure in said chamber and drawn into said bore with decreasing pressure thereby providing a visual and tactile indication of the pressure applied by the syringe, while relieving pressure in said chamber.

14. The syringe of claim 13 wherein said bore includes a threshold below said membrane for receiving said membrane when negative pressure in said chamber falls below a predetermined level.

15. An embolectomy catheter with an inflatable balloon at the distal end of the catheter including improved means for inflating the balloon, the improved inflating means comprising, in combination with the catheter;

a syringe including a hollow barrel which is closed at one end, a hollow tip at said closed end for conducting fluid between said syringe and the catheter, and a plunger mounted in said barrel for longitudinal movement therein, said plunger including piston means for sealingly engaging the inner surface of said barrel and an axial bore running from the distal to the proximal end of said plunger, said plunger further defining a chamber within said barrel between said closed end of said barrel and the distal end of said piston means; and, an elastomeric membrane closing the proximal end of said bore in said plunger, whereby said membrane is inflated with increasing pressure in said chamber and drawn into said bore with decreasing pressure thereby providing a visual and tactile indication of the pressure applied to the catheter by the syringe.

16. A method for injecting and withdrawing fluids while controlling the pressure being applied, comprising:

providing a syringe with an elastomeric membrane at the proximal end of the syringe barrel and in fluid communication with the chamber of the syringe;

applying sufficient pressure to the plunger of the syringe to inflate or deflate the membrane to a pre-determined position, and adjusting the pressure on the plunger to maintain the membrane at the pre-determined position.

17. An instrument for injecting and withdrawing fluids while providing an indication of the pressure applied thereby, comprising:

a hollow barrel which is closed at one end;

a plunger, mounted in said barrel for longitudinal movement therein, said plunger including piston means for sealingly engaging the inner surface of said barrel, said plunger defining a chamber within said barrel between said closed end of said barrel and said piston means said plunger further including a bore between said chamber and the proximal end of said plunger;

hollow tip means, disposed at said closed end of said barrel, for conducting fluid into and out of said chamber;

sensing means, in fluid communication with said chamber through said bore, said sensing means including an elastomeric membrane sealing said proximal end of said plunger which expands and contracts with increasing and decreasing pressure in said chamber; and a thumb loop provided at the proximal end of said plunger, said thumb loop including means for entrapping the edge of said membrane and sealing engagement with the proximal end of said plunger.

18. An instrument for injecting and withdrawing fluids while providing an indication of the pressure applied thereby, comprising:

a hollow barrel which is closed at one end;

a plunger, mounted in said barrel for longitudinal movement therein, said plunger including piston means for sealingly engaging the inner surface of said barrel, said plunger defining a chamber within said barrel between said closed end of said barrel and said piston means said plunger further including a bore between said chamber and the proximal end of said plunger;

hollow tip means, disposed at said closed end of said barrel, for conducting fluid into and out of said chamber;

sensing means, in fluid communication with said chamber through said bore, said sensing means including an elastomeric membrane sealing said proximal end of said plunger which expands and contracts with increasing and decreasing pressure in said chamber; and said bore including a threshold below said membrane for receiving said membrane when negative pressure in said chamber falls below a predetermined level.

* * * * *